United States Patent
Sharpless

(10) Patent No.: US 10,658,089 B2
(45) Date of Patent: May 19, 2020

(54) MOTION GUIDANCE ASSEMBLY FOR A COLLIMATOR DEVICE

(71) Applicant: UIH AMERICA, INC., Houston, TX (US)

(72) Inventor: Ronald Sharpless, Houston, TX (US)

(73) Assignee: UIH AMERICA, INC., Huston, TX (US)

( * ) Notice: Subject to any disclaimer, the term of this patent is extended or adjusted under 35 U.S.C. 154(b) by 49 days.

(21) Appl. No.: 16/147,732

(22) Filed: Sep. 29, 2018

(65) Prior Publication Data

US 2020/0105432 A1 Apr. 2, 2020

(51) Int. Cl.
*G21K 1/04* (2006.01)
*A61N 5/10* (2006.01)

(52) U.S. Cl.
CPC ........... *G21K 1/046* (2013.01); *A61N 5/1045* (2013.01); *A61N 5/1075* (2013.01)

(58) Field of Classification Search
CPC ..... A61N 5/1045; A61N 5/1075; G21K 1/046
See application file for complete search history.

(56) References Cited

U.S. PATENT DOCUMENTS

| 5,396,534 A | * | 3/1995 | Thomas | G21K 1/04 378/147 |
|---|---|---|---|---|
| 9,324,468 B2 | | 4/2016 | Mansfield et al. | |
| 9,406,411 B2 | | 8/2016 | Sayeh et al. | |
| 2009/0001295 A1 | * | 1/2009 | Johnsen | G21K 1/04 250/505.1 |
| 2015/0170778 A1 | | 6/2015 | Echner et al. | |

* cited by examiner

*Primary Examiner* — Mark R Gaworecki
(74) *Attorney, Agent, or Firm* — Metis IP LLC

(57) ABSTRACT

The present disclosure relates to a motion guidance assembly for guiding the motion of a collimator device. The motion guidance assembly may include a first pair of flexible plates connected to the collimator device. The first pair of flexible plates may be deformable in a direction perpendicular to an opening of the collimator device. A deformation of the first pair of flexible plates may guide the motion of the collimator device based on a driving force.

20 Claims, 8 Drawing Sheets

US 10,658,089 B2

MOTION GUIDANCE ASSEMBLY FOR A COLLIMATOR DEVICE

TECHNICAL FIELD

The present disclosure generally relates to a mechanical device, and more particularly, relates to a motion guidance assembly for guiding a movement of a collimator device.

BACKGROUND

A radiation system (e.g., a computed tomography (CT) scanner, a radiotherapy apparatus) may include a collimation assembly to reduce harmful radiation emitted from a radiation source. Application specific adjustments to the radiation reduction is achieved using the physical movement of a collimator device within the collimation assembly. The movement of the collimator device may be actuated and/or guided by a motion system. However, a traditional motion system typically has unintentional over constraints leading to unpredictable performance from varying friction over the lifetime of the system. Therefore, it is desirable to develop a friction free motion guidance assembly for guiding the movement of the collimator device.

SUMMARY

One aspect of the present disclosure relates to a motion guidance assembly for guiding the motion of a collimator device. The motion guidance assembly may include a first pair of flexible plates connected to the collimator device. The first pair of flexible plates may be deformable in a direction perpendicular to an opening of the collimator device. A deformation of the first pair of flexible plates may guide the motion of the collimator device based on a driving force.

Another aspect of the present disclosure relates to a collimation assembly. The collimation assembly may include a shielded box configured to collimate a plurality of radiation rays, a movable gate configured to adjust an opening size of the second opening, and/or a drive assembly configured to drive the movable gate to move. The shielded box may include a first opening and a second opening. The first opening may be configured to allow a first portion of the plurality of radiation rays to enter the collimation assembly. The second opening may be configured to allow a second portion of the plurality of radiation rays to leave the collimation assembly. The first portion of the plurality of radiation rays may include the second portion of the plurality of radiation rays. The movable gate may be connected to a first pair of flexible plates. A movement of the movable gate may be guided by the first pair of flexible plates. The drive assembly may be configured to drive the movable gate to move in a direction associated with a deformation of the first pair of flexible plates.

A further aspect of the present disclosure relates to a radiation imaging system. The radiation imaging system may include: a radiation source configured to emit radiation rays; a collimation assembly configured to collimate the emitted radiation rays; one or more radiation detectors configured to generate measurement data in response to at least a portion of the emitted radiation rays; a controller configured to control one or more of the radiation source, the collimation assembly and the one or more radiation detectors; and/or one or more processors configured to generate an image based on the measurement data. The collimation assembly may include: a shielded box configured to collimate a plurality of radiation rays, the shielded box including a first opening and a second opening, the first opening being configured to allow a first portion of the plurality of radiation rays to enter the collimation assembly, the second opening being configured to allow a second portion of the plurality of radiation rays to leave the collimation assembly, the first portion of the plurality of radiation rays including the second portion of the plurality of radiation rays; a movable gate configured to adjust an opening size of the second opening, the movable gate being connected to a first pair of flexible plates, a movement of the movable gate being guided by the first pair of flexible plates; and/or a drive assembly configured to drive the movable gate to move in a direction associated with a deformation of the first pair of flexible plates.

In some embodiments, the first pair of flexible plates may include a first flexible plate and a second flexible plate, the first flexible plate and the second flexible plate having a same dimension and including a same material.

In some embodiments, the first flexible plate and the second flexible plate may be positioned in parallel on opposite sides of the collimator device.

In some embodiments, the first flexible plate and the second flexible plate may be positioned in parallel on a same side of the collimator device.

In some embodiments, a first end of each flexible plate of the first pair of flexible plates may be connected to a first end of the collimator device; and/or a second end of each flexible plate of the first pair of flexible plates may be fixed onto a base frame.

In some embodiments, a connector may be connected to the first end of the collimator device, wherein the connector being configured to transmit the driving force to the collimator device to drive the motion of the collimator device.

In some embodiments, the motion guidance assembly may further include a second pair of flexible plates connected to the collimator device. The second pair of flexible plates may be deformable in the direction perpendicular to the opening of the collimator device.

In some embodiments, the second pair of flexible plates may include a third flexible plate and a fourth flexible plate, the third flexible plate and the fourth flexible plate being positioned in parallel on opposite sides of the collimator device.

In some embodiments, a first end of each flexible plate of the first pair of flexible plates may be connected to a first end of the collimator device; a second end of each flexible plate of the first pair of flexible plates may be fixed onto a base frame; a first end of each flexible plate of the second pair of flexible plates may be connected to a second end of the collimator device; a second end of each flexible plate of the second pair of flexible plates may be fixed onto the base frame; and/or a connector may be connected to a side of the collimator device, a distance between the connector and the first end of the collimator device being substantially the same as a distance between the connector and the second end of the collimator device, the connector being configured to transmit the driving force to the collimator device to drive the motion of the collimator device.

In some embodiments, a stress point on the connector associated with the driving force may be at a substantially half height of each flexible plate of the first pair of flexible plates or the second pair of flexible plates.

In some embodiments, the motion guidance assembly may further include a third pair of flexible plates deformable in the direction perpendicular to the opening of the collimator device. A first end of each flexible plate of the first pair of flexible plates may be connected to a first end of the collimator device. A first end of each flexible plate of the third pair of flexible plates may be fixed onto a base frame. A second end of each flexible plate of the first pair of flexible plates and a second end of each flexible plate of the third pair of flexible plates may be connected through a first connecting piece.

In some embodiments, the third pair of flexible plates and one flexible plate of the first pair of flexible plates may be positioned on a same side of the collimator device, while another flexible plate of the first pair of flexible plates is positioned on an opposite side of the collimator device.

In some embodiments, the motion guidance assembly may further include a second pair of flexible plates and a fourth pair of flexible plates, the second pair of flexible plates and the fourth pair of flexible plates being deformable in the direction perpendicular to the opening of the collimator device. A first end of each flexible plate of the second pair of flexible plates may be connected to a second end of the collimator device. A first end of each flexible plate of the fourth pair of flexible plates may be fixed onto the base frame. A second end of each flexible plate of the second pair of flexible plates and a second end of each flexible plate of the fourth pair of flexible plates may be connected to a second connecting piece.

In some embodiments, the first pair of flexible plates may include spring steel plates.

In some embodiments, the collimator device may be an adjustable gate or an adjustable filter.

In some embodiments, the first pair of flexible plates may include a first flexible plate and a second flexible plate, the first flexible plate and the second flexible plate having a same dimension and including a same material. The first flexible plate and the second flexible plate may be positioned in parallel on opposite sides of the movable gate.

In some embodiments, a first end of the movable gate may be connected to a first end of each flexible plate of the first pair of flexible plates. A second end of each flexible plate of the first pair of flexible plates may be fixed onto a base frame. A connector may be connected to the first end of the movable gate, the connector being configured to transmit a driving force generated by the drive assembly to the movable gate to drive the movable gate to move.

In some embodiments, the movable gate may be further connected to a second pair of flexible plates. The second pair of flexible plates may include a third flexible plate and a fourth flexible plate, the third flexible plate and the fourth flexible plate being positioned in parallel on opposite sides of the movable gate.

In some embodiments, a first end of the movable gate may be connected to a first end of each flexible plate of the first pair of flexible plates. A second end of each flexible plate of the first pair of flexible plates may be fixed onto a base frame. A second end of the movable gate may be connected to a first end of each flexible plate of the second pair of flexible plates. A second end of each flexible plate of the second pair of flexible plates may be fixed onto the base frame. A connector may be connected to a side of the movable gate, a distance between the connector and the first end of the movable gate being substantially the same as a distance between the connector and the second end of the movable gate, the connector being configured to transmit a driving force generated by the drive assembly to the movable gate to drive the movable gate to move.

In some embodiments, the collimation assembly may further include a connector and a transmission part. The connector may be configured to transmit a driving force generated by the drive assembly to the movable gate to drive the movable gate to move. The transmission part may be configured to transmit the driving force from the drive assembly to the connector.

In some embodiments, the transmission part may be a rod flexure or a plate, a normal of the plate being in a direction that is substantially perpendicular to the driving force.

In some embodiments, a stress point on the connector associated with the driving force generated by the drive assembly may be at a substantially half height of each flexible plate of the first pair of flexible plates.

In some embodiments, the drive assembly may include a linear motor or a piezoelectric actuator.

In some embodiments, the first pair of flexible plates may include an elastic material.

In some embodiments, the collimation assembly may further include an additional gate, the additional gate being the same as the movable gate and positioned parallel to the movable gate and on a same plane of the movable gate.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
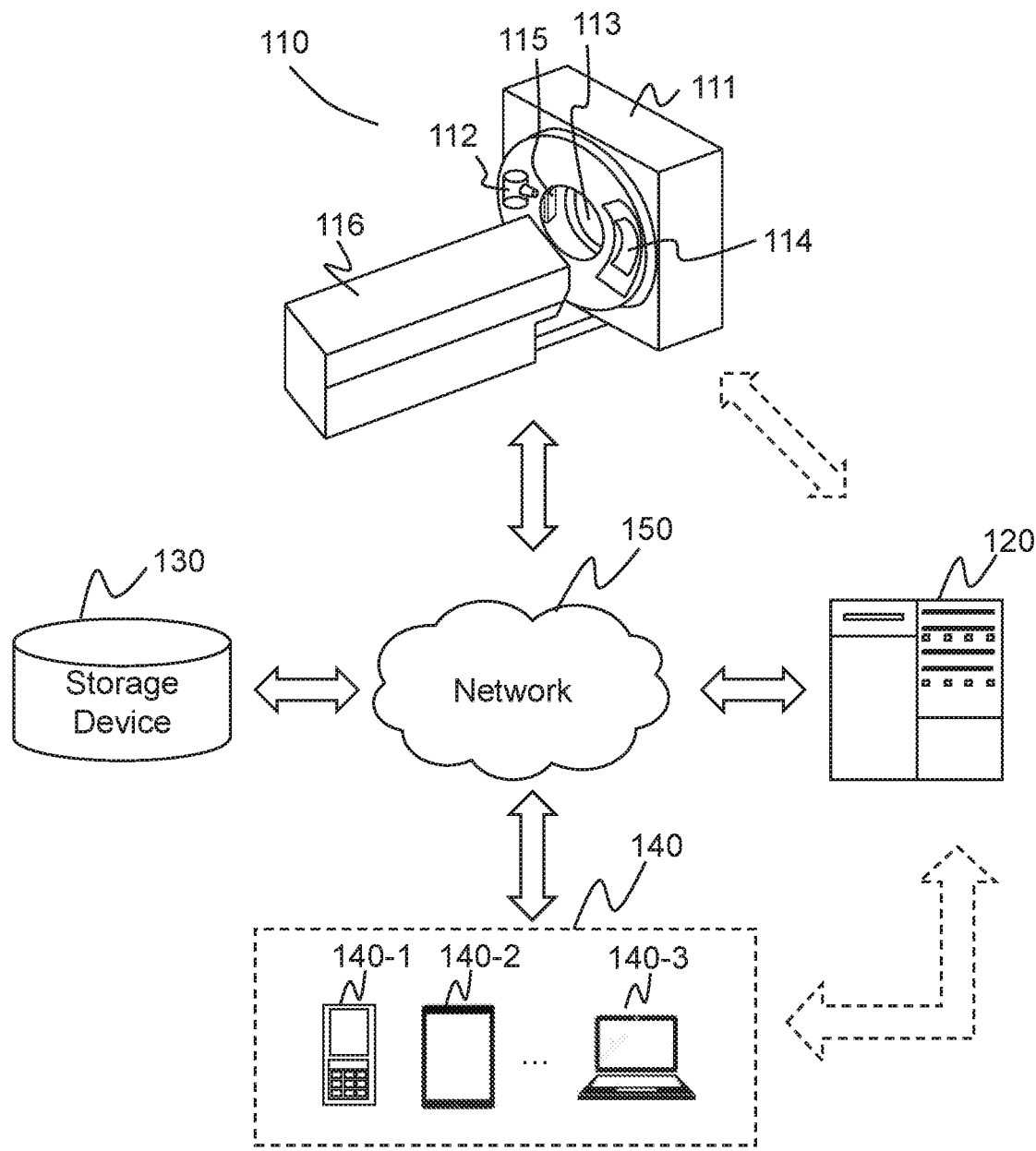
FIG. 1 is a schematic diagram illustrating an exemplary imaging system according to some embodiments of the present disclosure.

In the following detailed description; numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following descriptions are provided with reference to a motion guidance assembly, a collimation assembly, and/or a radiation imaging system. It is understood that this is not intended to limit the scope of the present disclosure. For persons having ordinary skill in the art, a certain amount of variations, changes and/or modifications may be deducted under the guidance of the present disclosure. Those variations, changes and/or modifications do not depart from the scope of the present disclosure.

FIG. 1 is a schematic diagram illustrating an exemplary imaging system according to some embodiments of the present disclosure. As shown in FIG. 1, the imaging system 100 may include a scanner 110, a network 150, one or more terminals 140, a processing device 120, and a storage device 130. The components in the imaging system 100 may be connected in one or more of various ways. Merely by way of example, as illustrated in FIG. 1, the scanner 110 may be connected to the processing device 120 through the network 150. As another example, the scanner 110 may be connected to the processing device 120 directly as indicated by the bi-directional arrow in dotted lines linking the scanner 110 and the processing device 120. As a further example, the storage device 130 may be connected to the processing device 120 directly or through the network 150. As still a further example, one or more terminals 140 may be connected to the processing device 120 directly (as indicated by the bi-directional arrow in dotted lines linking the terminal 140 and the processing device 120) or through the network 150.

The scanner 110 may generate or provide image data via scanning a subject or a part of the subject. The scanner 110 may include a single-modality scanner and/or a multi-modality scanner. The single-modality scanner may include, for example, a computed tomography (CT) scanner, a positron emission tomography (PET) scanner, or an X-ray scanner. In some embodiments, the CT scanner may be a spiral CT scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, a digital radiography (DR) device, a radiotherapy (RT) device, or the like, or a combination thereof. In some embodiments, the subject may include a body, a substance, an object, or the like, or a combination thereof. In some embodiments, the subject may include a specific portion of a body, such as a head, a thorax, an abdomen, or the like, or a combination thereof.

In some embodiments, the scanner 110 may include a gantry 111, a radiation source 112, one or more radiation detectors 114, a detecting region 113, a collimation assembly 115, and a table 116. The gantry 111 may support the radiation source 112, the radiation detector(s) 114, and the collimation assembly 115. The radiation source 112 may include a tube (e.g., an X-ray tube) configured to generate and/or emit one or more radiation rays traveling toward the subject located on the table 116. In some embodiments, the radiation source 112 may include a cold cathode ion tube, a high vacuum hot cathode tube, a rotating anode tube, etc. The radiation rays may include a particle ray, a photon ray, or the like, or a combination thereof.

The radiation detectors 114 may be configured to detect one or more radiation rays emitted from the radiation source 112. In some embodiments, the radiation detectors 114 may include one or more rows of detectors. One row may include a plurality of detectors (also referred to as channels). Thus, the radiation detectors 114 may include a plurality of detectors arranged in a row direction and a channel direction along an annular inner wall of the detecting region 113. As used herein, the row direction may be parallel to a central axis of the detecting region 113 (e.g., a direction along which the table 116 may enter into the detecting region 113). The channel direction may be perpendicular to the row direction in a three-dimensional space of the detecting region 113. For example, the channel direction may be the circular direction of the annular inner wall of the detecting region 113. A detector in the radiation detectors 114 may have any suitable shape. For example, the radiation detector may have the shape of an arc, a circle, a rectangle, or the like, or a combination thereof.

In some embodiments, when the radiation source 112 emits a plurality of radiation rays traversing the subject, the radiation detectors 114 may detect the traversed radiation rays and generate raw data (e.g., projection data, or measurement data) related to the subject. The collimation assembly 115 may collimate the radiation rays that emit from the radiation source 112 or travel toward the radiation detectors 114. More descriptions of the collimation assembly 115 may be found elsewhere in the present disclosure (e.g., FIG. 2 and the description thereof). A detector in the radiation detectors 114 may detect one or more radiation rays and generate a subset of the raw data. In some embodiments, an image corresponding to a slice of the subject may be reconstructed based on raw data generated by one row of detectors. In some embodiments, an image corresponding to a slice of the subject may be reconstructed based on raw data generated by more than one row of detectors.

The processing device 120 may process data and/or information obtained from the scanner 110, the storage device 130, and/or the terminal(s) 140. For example, the processing device 120 may reconstruct an image based on projection data (or measurement data) collected or generated by the scanner 110 (e.g., the radiation detectors 114). As another example, the processing device 120 may transmit an instruction to the collimation assembly 115 to collimate the radiation rays. In some embodiments, the processing device 120 may be a single server or a server group. The server group may be centralized or distributed. In some embodiments, the processing device 120 may be local or remote. For example, the processing device 120 may access information and/or data from the scanner 110, the storage device 130, and/or the terminal(s) 140 via the network 150. As another example, the processing device 120 may be directly connected to the scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage device 130 may store data, instructions, and/or any other information. In some embodiments, the storage device 130 may store data obtained from the processing device 120, the terminal(s) 140, and/or the scanner 110. In some embodiments, the storage device 130 may store data and/or instructions that the processing device 120 may execute or use to perform exemplary methods described in the present disclosure. In some embodiments, the storage device 130 may include a mass storage, removable storage, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the imaging system 100 (e.g., the processing device 120, the terminal(s) 140, etc.). One or more components of the imaging system 100 may access the data or instructions stored in the storage device 130 via the network 150. In some embodiments, the storage device 130 may be part of the processing device 120.

The terminal(s) 140 may be connected to and/or communicate with the scanner 110, the processing device 120, and/or the storage device 130. For example, the terminal(s) 140 may obtain a processed image from the processing device 120. As another example, the terminal(s) 140 may obtain image data acquired via the scanner 110 and transmit the image data to the processing device 120 to be processed. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the scanner 110, the processing device 120, the storage device 130, the terminal(s) 140, etc.) may communicate information and/or data with one or more other components of the imaging system 100 via the network 150. For example, the processing device 120 may obtain image data from the scanner 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as public cloud, private cloud, community, and hybrid clouds, etc. However, those variations and modifications do not depart the scope of the present disclosure.

Figure 2:
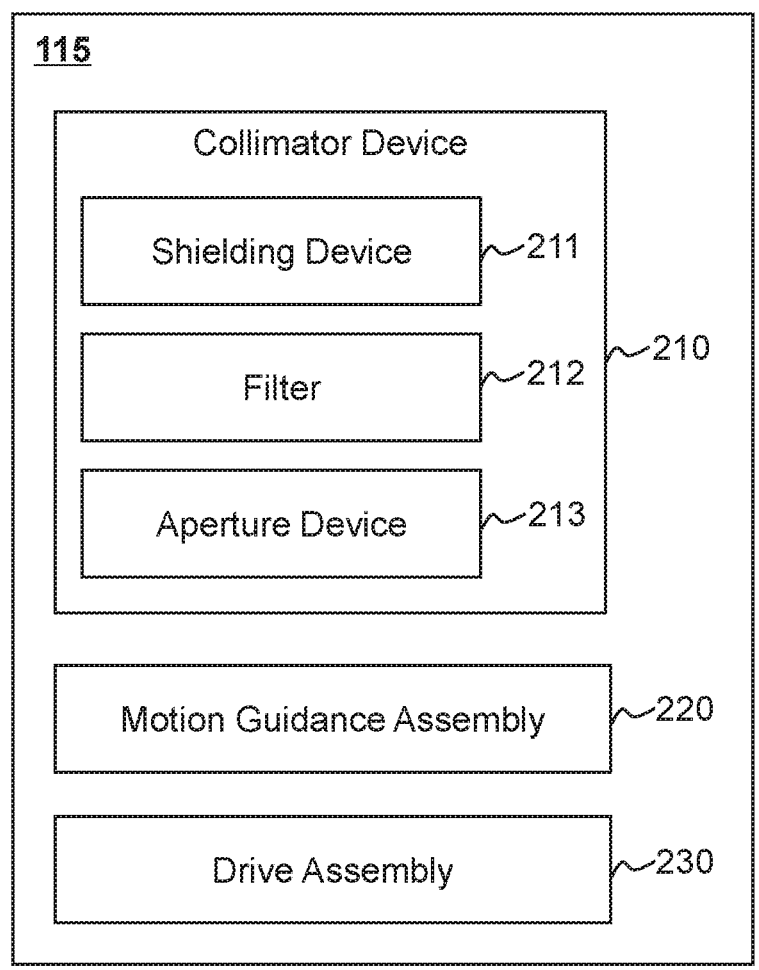
FIG. 2 is a schematic diagram illustrating components of an exemplary collimation assembly according to some embodiments of the present disclosure.

FIG. 2 is a schematic diagram illustrating components of an exemplary collimation assembly according to some embodiments of the present disclosure. As illustrated in FIG. 2, the collimation assembly 115 may include a collimator device 210, a motion guidance assembly 220, and a drive assembly 230.

The collimator device 210 may be configured to narrow or adjust one or more beams of particles or waves. In some embodiments, the collimator device 210 may cause the direction of one or more beams of particles or waves to become more aligned in a specific direction. That is, the beams of particles or waves passing through the collimator device 210 may become one or more collimated or parallel rays. In some embodiments, the collimator device 210 may cause the spatial cross section of the beams of particles or waves passing through the collimator device 210 to become smaller. In some embodiments, the collimator device 210 may filter the beams of particles or waves so that only a portion of the beams that travel parallel to a specified direction are allowed to pass through the collimator device 210.

In some embodiments, the collimator device 210 may include a shielding device 211, a filter 212, an aperture device 213, or the like, or a combination thereof. The shielding device 211 may be configured to collimate a plurality of radiation rays. In some embodiments, the shielding device 211 may be a shielded box (e.g., the shielded box 360 illustrated in FIG. 3). The shielding device 211 may include a first opening and a second opening. The first opening of the shielding device 211 may allow a first portion of the plurality of radiation rays to enter the collimation assembly 115. The second opening may allow a second portion of the plurality of radiation rays to leave the collimation assembly 115. In some embodiments, the first portion of the plurality of radiation rays may include the second portion of the plurality of radiation rays. The filter 212 may be configured to shape the radiation rays that enter the collimation assembly 115. In some embodiments, the filter 212 may reduce a radiation dose of the radiation rays that leave the collimation assembly 115. In some embodiments, the position of the filter 212 may be adjusted. In some embodiments, the movement of the filter 212 may be guided by the motion guidance assembly 220. The aperture device 213 may be configured to adjust the opening size of the first opening and/or the second opening of the shielding device 211. In some embodiments, the aperture device 213 may include one or more movable gates. In some embodiments, the position of the movable gate(s) may be adjusted. In some embodiments, the movement of the movable gate(s) may be guided by the motion guidance assembly 220. More descriptions regarding the collimator device 210 may be found elsewhere in the present disclosure (e.g., FIG. 3 and the descriptions thereof).

The motion guidance assembly 220 may be configured to guide the movement of one or more components (e.g., the filter 212, a movable gate, or the like) of the collimator device 210. In some embodiments, the motion guidance assembly 220 may include a linear guide and a linear slider. For example, the linear slider may be connected to the collimator device 210. The linear slider may be driven to move on the linear guide based on a driving force. The movement of the linear slider on the linear guide may guide the movement of the collimator device 210.

In some embodiments, the motion guidance assembly 220 may include one or more flexible plates. In some embodiments, the flexible plate(s) may be connected to the collimator device 210. In some embodiments, the flexible plate(s) may be deformable in a direction perpendicular to an elongated opening of the collimator device 210. The deformation of the flexible plate(s), based on a driving force, may guide the movement of the collimator device 210.

In some embodiments, the flexible plate(s) may be stiff in one or more degrees except the deformable direction. With the use of the flexible plate(s), the collimation assembly 115 may not be over constrained. In some embodiments, there may be no relative motion between contacting component of the collimation assembly 115. With the use of the flexible plate(s), no severe wear may be produced in the collimation assembly 115. In some embodiments, with the use of the flexible plate(s), elastic potential energy may be built based on the deformation of the flexible plate(s), which may assist the drive assembly 230 during acceleration and/or deceleration. In some embodiments, with the use of the flexible plate(s), connections to the stationary frame are fixed and permanent, and accordingly, there may be no guidance backlash (or hysteresis) during the movement of the collimator device 210. In some embodiments, with the use of the flexible plate(s) and/or a transmission part (e.g., a rod flexure, see FIG. 5), there may be a spring-load giving preload to the drive assembly 230, which may reduce the drive backlash (or hysteresis).

Figure 3:
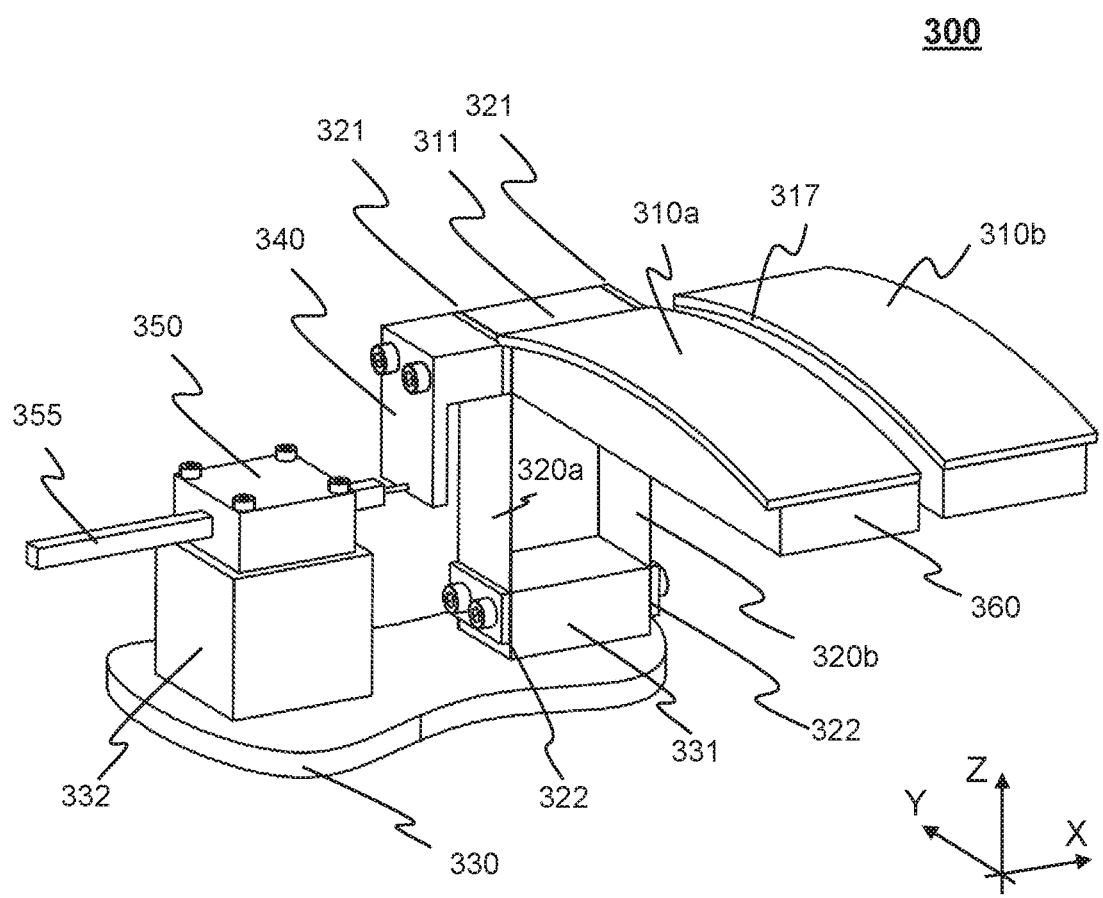
FIG. 3 is a schematic diagram illustrating an exemplary collimation assembly including a motion guidance assembly according to some embodiments of the present disclosure.
Figure 6:
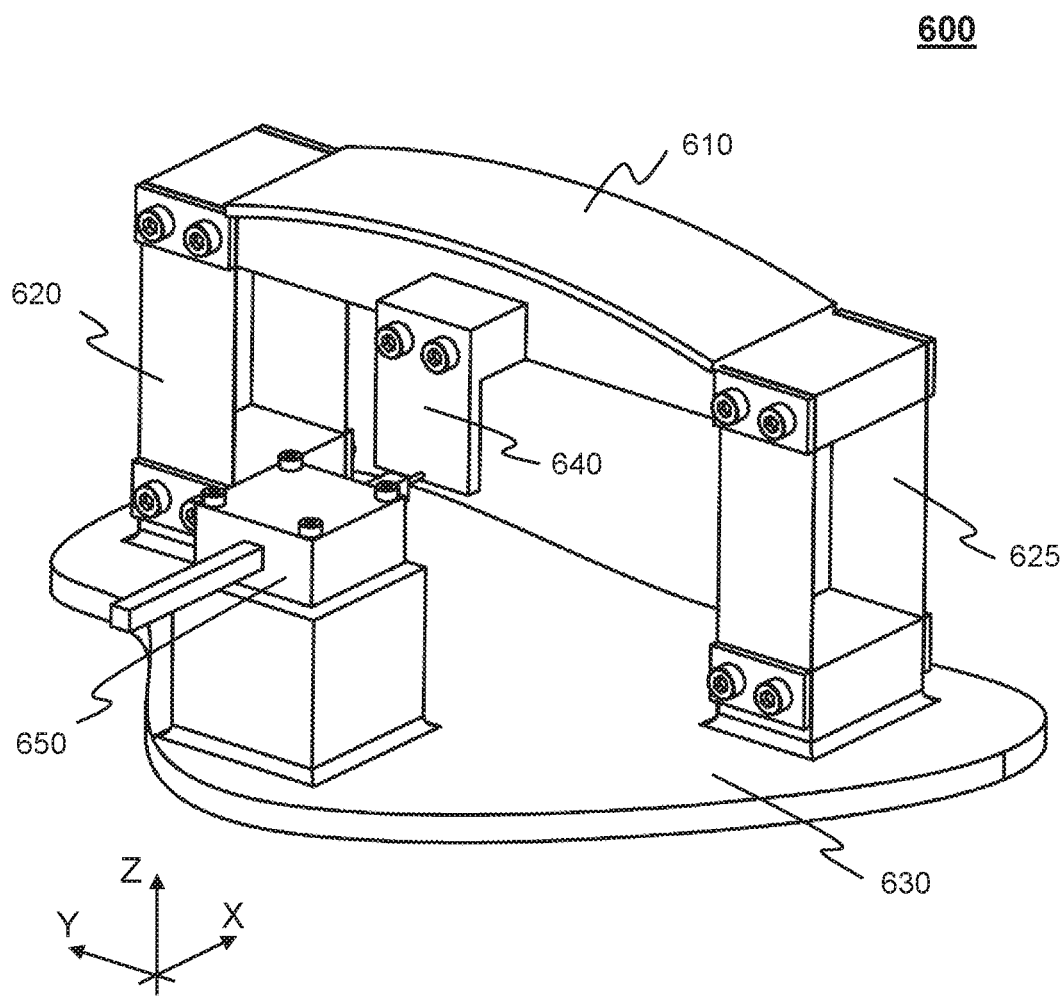
FIG. 6 is a schematic diagram illustrating an exemplary collimation assembly according to some embodiments of the present disclosure.
Figure 7:
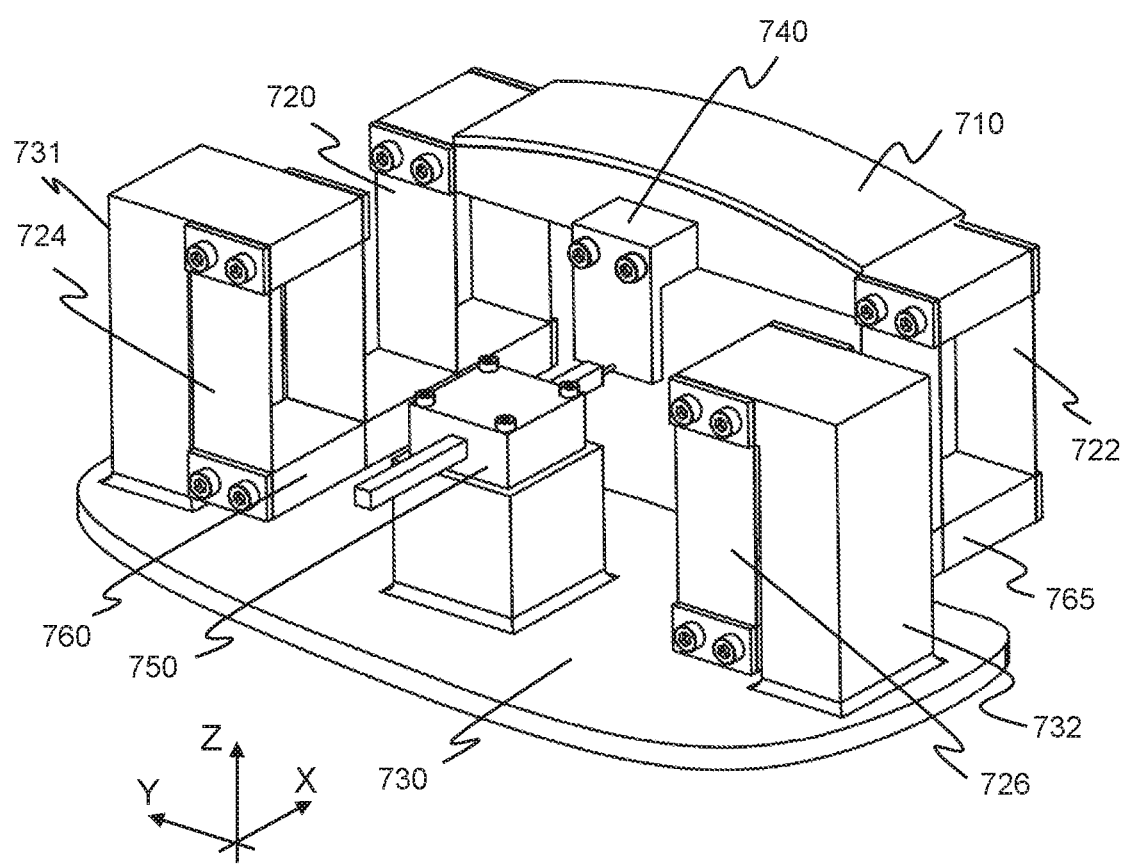
FIG. 7 is a schematic diagram illustrating an exemplary collimation assembly according to some embodiments of the present disclosure.
Figure 8:
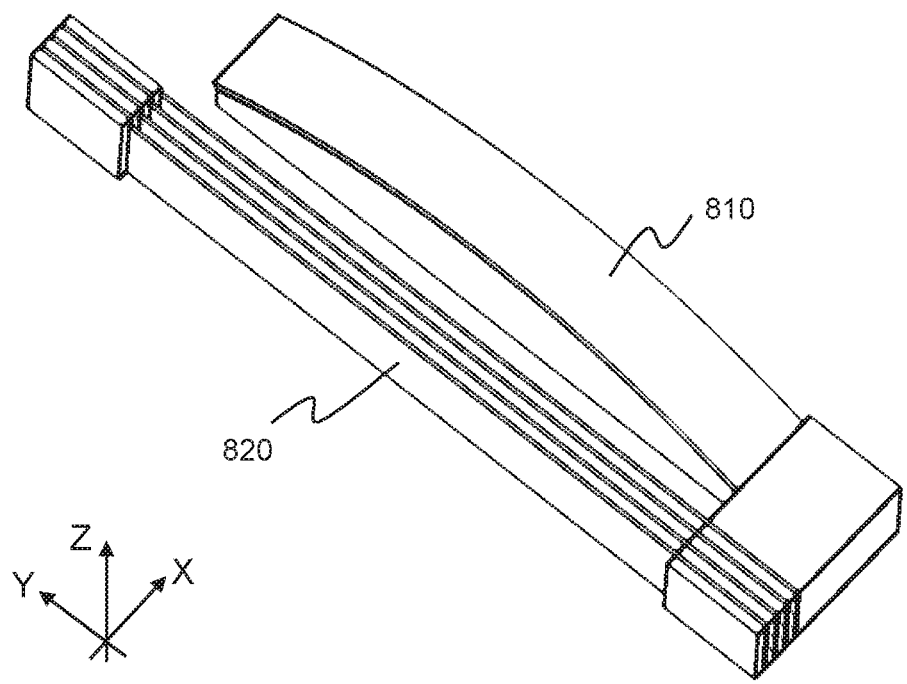
FIG. 8 is a schematic diagram illustrating an exemplary collimation assembly according to some embodiments of the present disclosure.

Exemplary motion guidance assemblies may include the pair of flexible plates shown in FIG. 3, the pairs of flexible plates 620, 625 shown in FIG. 6, the pairs of flexible plates 720, 722, 724, 726 shown in FIG. 7, and/or the group of flexible plates 820 shown in FIG. 8. More descriptions regarding the motion guidance assembly 220 may be found elsewhere in the present disclosure (e.g., FIGS. 3, 4, and 6-8, and the descriptions thereof).

The drive assembly 230 may be configured to generate a force for movement of one or more components (e.g., the shielding device 211, the filter 212, the aperature device 213, a movable gate, or the like) of the collimator device 210. The force for movement of the component(s) of the collimator device 210 may also be referred to as a driving force. The driving force may include either a pulling force or a pushing force along the movement direction of the one or more components of the collimator device 210. In some embodiments, the drive assembly 230 may be any device that can generate the driving force. For example, the drive assembly 230 may include a direct-driven screw, a direct-driven mandrel, a linear motor, a piezoelectric actuator, or the like, or a combination thereof. More descriptions regarding the drive assembly 230 may be found elsewhere in the present disclosure (e.g., FIGS. 3 and 5-7, and the descriptions thereof). In some embodiments, with the use of the piezoelectric actuator, the drive assembly 230 may be self-locked, without relying on external power or control for maintaining a stationary position. In some embodiments, with the use of the piezoelectric actuator, the drive assembly 230 may have controllability robustness since the load inertia may be relatively low. In some embodiments, with the use of the piezoelectric actuator, the acceleration and/or deceleration of the drive assembly 230 may be relatively fast. In some embodiments, with the use of the piezoelectric actuator, the resolution of the drive assembly 230 may be relatively high, and accordingly, the control accuracy of the collimator device 210 may be relatively high, which may make dose savings possible.

It should be noted that the above description of the collimation assembly 115 is merely provided for the purposes of illustration and not intended to limit the scope of the present disclosure. For persons having ordinary skill in the art, multiple variations and modifications may be made under the teachings of the present disclosure. However, those variations and modifications do not depart from the scope of the present disclosure. For example, the filter 212 may be omitted. As another example, the motion guidance assembly 220 and/or the drive assembly 230 may be connected to the gantry 111.

FIG. 3 is a schematic diagram illustrating an exemplary collimation assembly including a motion guidance assembly according to some embodiments of the present disclosure. As shown in FIG. 3, the collimation assembly 300 may include an aperature device (e.g., the first movable gate 310*a*), a pair of flexible plates (including a first flexible plate 320*a* and a second flexible plate 320*b*), a base frame 330, a connector 340, and a drive assembly 350. The drive assembly 350 may include a motor plunger 355.

The aperature device may be configured to narrow or adjust one or more beams of particles or waves. In some embodiments, the beams of particles or waves are also referred to herein as radiation rays. A radiation ray may include, for example, a particle ray, a photon ray, or the like, or a combination thereof. The particle ray may include neutron, proton, electron, μ-meson, heavy ion, or the like, or a combination thereof. The photon ray may include an X-ray, a γ-ray, an α-ray, a β-ray, an ultraviolet ray, a laser, or the like, or a combination thereof. In some embodiments, the photon ray may be an X-ray, and the scanner 110 may be a CT imaging device, a digital radiography (DR) device, a radiotherapy (RT) device, a multi-modality system, or the like, or a combination thereof. An exemplary multi-modality system may be a computed tomography-positron emission tomography (CT-PET) system. In some embodiments, the aperature device may cause the direction of one or more beams of particles or waves to become more aligned in a specific direction. That is, the beams of particles or waves passing through the aperature device may become one or more collimated or parallel rays. In some embodiments, the aperature device may cause a spatial cross section of the beams of particles or waves passing through the aperature device to become smaller. In some embodiments, the aperature device may filter the beams of particles or waves so that only a portion of the beams that travel parallel to a specified direction are allowed to pass through the aperature device.

In some embodiments, a collimator device may include the aperature device, a shielded box, one or more movable gates, a filter (e.g., a flat filter, a bowtie filter), or the like, or a combination thereof. In some embodiments, the shielded box may be configured to collimate a plurality of radiation rays. The shielded box may include a first opening and a second opening. The first opening of the shielded box may allow a first portion of the plurality of radiation rays to enter the collimation assembly 300. The second opening may allow a second portion of the plurality of radiation rays to leave the collimation assembly 300. In some embodiments, the first portion of the plurality of radiation rays may include the second portion of the plurality of radiation rays. In some embodiments, the first portion of the plurality of radiation rays may further include a third portion of the plurality of radiation rays. In some embodiments, the shielded box may not allow the third portion of the plurality of radiation rays to escape elsewhere. The shielded box may be made of a material including lead, barium, wolfram, iron, copper, or the like, or any compound thereof.

In some embodiments, the one or more movable gates may be configured to adjust the opening size of the first opening and/or the second opening. In some embodiments, the position of the movable gate(s) may be adjusted. In some embodiments, the movement of the movable gate(s) may be guided by a motion guidance assembly (e.g., the pair of flexible plates). The movable gate(s) may be made of a material including lead, barium, wolfram, iron, copper, or the like, or any compound thereof.

In some embodiments, the filter may be configured to shape the radiation rays that enter the collimation assembly 300. In some embodiments, the filter may reduce a radiation dose of the radiation rays that leave the collimation assembly 300. For example, in a CT imaging device, the filter may reduce X-ray energies that reach a subject (e.g., a patient) by removing long-wavelength X-rays. As another example, in the CT imaging device, the filter may make an intensity of the radiation rays to become more uniform, so that artifacts may be reduced in a generated CT image. In some embodiments, the filter may be a piece of metal or alloy. The filter may be made of a material including beryllium, aluminum, copper, poly-methyl methacrylate (PMMA), polyethylene, teflon, beryllium oxide (BeO), boron carbide ($B_4C$), or the like, or any compound thereof. In some embodiments, the position of the filter may be adjusted. In some embodiments, the movement of the filter may be guided by a motion guidance assembly (e.g., the pair of flexible plates).

In some embodiments, the motion guidance assembly may include one or more flexible plates (e.g., the pair of flexible plates). The pair of flexible plates may be configured to guide the movement of the collimator device (e.g., the movable gate(s), the filter). FIG. 3 illustrates an exemplary motion guidance assembly for guiding the movement of a movable gate. In some embodiments, the aperature device may include a first movable gate 310a and/or a second gate 310b (i.e., an additional gate). In some embodiments, the second gate 310b may be the same as or different from the first movable gate 310a. In some embodiments, the second gate 310b may be positioned parallel to the first movable gate 310a. In some embodiments, the second gate 310b may be positioned on the same plane of the first movable gate 310a. In some embodiments, there may be an elongated opening 317 between the first movable gate 310a and the second gate 310b. In some embodiments, the first movable gate 310a may be positioned mirror symmetrical to the second gate 310b with respect to the elongated opening 317. In some embodiments, the first movable gate 310a may be positioned central symmetric to the second gate 310b with respect to a center point of the elongated opening 317, In some embodiments, the opening size of the elongated opening 317 may be adjusted by moving the first movable gate 310a and/or the second gate 310b. As shown in FIG. 3, the aperature device (e.g., the first movable gate 310a) may be connected to a pair of flexible plates. In some embodiments, the additional gate may be immovable. For example, the additional gate may be fixed onto the gantry 111. Alternatively, the additional gate may be movable. It should be noted that FIG. 3 is merely provided for the purpose of illustration, and not intended to limit the scope of the present disclosure. For example, the second gate 310b may be connected to an additional pair of flexible plates and/or an additional drive assembly (not shown in FIG. 3). The additional pair of flexible plates may be similar to the pair of flexible plates. The additional drive assembly may be similar to the drive assembly 350.

As shown in FIG. 3, the pair of flexible plates may include a first flexible plate 320a and/or a second flexible plate 320b. In some embodiments, the first flexible plate 320a and the second flexible plate 320b may have the same dimension. In some embodiments, the first flexible plate 320a and the second flexible plate 320b may include the same material. In one embodiment, as shown in FIG. 3, the first flexible plate 320a and the second flexible plate 320b may be positioned in parallel on opposite sides of the aperature device. In other embodiments (e.g., as shown in FIG. 8), the first flexible plate 320a and the second flexible plate 320b may be positioned in parallel on the same side of the aperature device.

As illustrated in FIG. 3, a first end 321 of each flexible plate of the pair of flexible plates may be connected to a first end 311 of the first movable gate 310a, In some embodiments, the first end 321 of each flexible plate of the pair of flexible plates may be fixed onto the first end 311 of the first movable gate 310a through a, for example, glue joint, bonding, bolted connection, or the like, or a combination thereof. A second end 322 of each flexible plate of the pair of flexible plates may be fixed onto the base frame 330. The second end 322 of each flexible plate of the pair of flexible plates may be fixed onto the base frame 330 through a, for example, glue joint, bonding, bolted connection, or the like, or a combination thereof. In some embodiments, the second end 322 of each flexible plate of the pair of flexible plates may be fixed onto the base frame 330 via a connecting piece 331. In some embodiments, the base frame 330 may be connected to the gantry 111. For example, the base frame 330 may be fixed onto the gantry 111. As another example, the base frame 330 may be an integrated part of the gantry 111.

The drive assembly 350 may be configured to generate a driving force to drive the first movable gate 310a to move. As shown in FIG. 3, the first movable gate 310a may be driven to move along the X-axis direction. The driving force may include either a pulling force or a pushing force along the movement direction of the first movable gate 310a. In some embodiments, the drive assembly 350 may be any device that can generate the driving force. For example, the drive assembly 350 may include a direct-driven screw, a direct-driven mandrel, a linear motor, a piezoelectric actuator, or the like, or a combination thereof. In some embodiments, the drive assembly 350 may include a motor plunger 355. The motor plunger 355 may be driven by the drive assembly 350 to move along the X-axis direction. The motor plunger 355 may transmit the driving force to the first movable gate 310a to drive the first movable gate 310a to move.

In some embodiments, the driving force generated by the drive assembly 350 may be applied directly to the first movable gate 310a to drive the movement of the first movable gate 310a. For example, the driving force may be applied to the first end 311 of the first movable gate 310a. In some embodiments, a connector (e.g., the connector 340) may be connected to the first movable gate 310a to transmit the driving force to the first movable gate 310a to drive the movement of the first movable gate 310a. For example, as shown in FIG. 3, the connector 340 may be connected to the first end 311 of the first movable gate 310a. In some embodiments, the connector 340 may be made of a hard material, such as aluminum, steel, alloy, plastic, or the like, or a combination thereof. The connector 340 may have a shape of a block, a sheet, etc. For example, as shown in FIG. 3, the connector 340 may include a right-angle block. In some embodiments, the connector 340 may be connected to the first movable gate 310a through a, for example, glue joint, bonding, bolted connection, or the like, or a combination thereof. In some embodiments, the connector 340 and the first movable gate 310a may form a single piece. The drive assembly 350 may actuate the motor plunger 355 to move, and then the motor plunger 355 may transmit the driving force directly to the first movable gate 310a or via the connector 340. In some embodiments, the connector 340 may be an integrated part of the drive assembly 350. More descriptions regarding the drive assembly 350 may be found elsewhere in the present disclosure (e.g., FIG. 5 and the description thereof).

In some embodiments, the pair of flexible plates may be deformable in a direction perpendicular to the elongated opening 317 of the aperature device. As shown in FIG. 3, the elongated opening 317 of the aperature device may be parallel to the Y-axis direction. The pair of flexible plates may be deformable in the X-axis direction upon the first movable gate 310a being driven to move along the X-axis direction. As the second end 322 of each flexible plate of the pair of flexible plates are fixed onto the base frame 330, the first end 321 of each flexible plate of the pair of flexible plates may move along the X-axis direction with the movement of the first movable gate 310a. A relative displacement may be produced between the first end 321 and the second end 322 of each flexible plate of the pair of flexible plates, so that the pair of flexible plates may deform. In some embodiments, the deformation of the pair of flexible plates, based on a driving force, may guide the movement of the first movable gate 310a. More descriptions regarding the deformation of the pair of flexible plates may be found elsewhere in the present disclosure (e.g., FIGS. 4A and 4B and the descriptions thereof).

In some embodiments, one or more control modules (not shown) or controllers (not shown) may control the operation of the collimation assembly 300. The one or more control modules or controllers may be implemented as software and/or hardware modules and may be stored in any type of non-transitory computer-readable medium or other storage device. For example, the control modules may be stored in the processing device 120. In some embodiments, a software module may be compiled and linked into an executable program. It will be appreciated that software modules can be callable from other modules or from themselves, and/or can be invoked in response to detected events or interrupts. Software modules configured for execution on computing devices (e.g., a processor of computing device 120) can be provided on a computer-readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in a firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules, but can be represented in hardware or firmware. In general, the modules described herein refer to logical modules that can be combined with other modules or divided into sub-modules despite their physical organization or storage. In some embodiments, the one or more control modules or controllers may include signal processing circuitry, memory circuitry, one or more processors, a single chip microcomputer, or the like, or a combination thereof. In some embodiments, at least a portion of the one or more control modules or controllers may be integrated in one or more printed circuit boards of the scanner 110.

In some embodiments, the one or more control modules or controllers may send a motion instruction to the drive assembly 350. In response, the drive assembly 350 may actuate the motor plunger 355 to transmit the driving force to the first movable gate 310a (or the connector 340) based on the motion instruction received. The first movable gate 310a may be moved according to the driving force and guided by the deformation of the pair of flexible plates. Therefore, the opening size of the second opening of the shielded box may be adjusted based on the motion of the first movable gate 310a. In some embodiments, the one or more control modules or controllers may control the operation of the radiation source 112. In some embodiments, the one or more control modules or controllers may control the operation of one or more of the radiation detectors 114.

It should be noted that the above description of the collimation assembly 300 is merely provided for the purposes of illustration and not intended to limit the scope of the present disclosure. For persons having ordinary skill in the art, multiple variations and modifications may be made under the teachings of the present disclosure. However, those variations and modifications do not depart from the scope of the present disclosure. For example, there may be only one flexible plate for guiding the movement of the aperature device. As another example, there may be two or more (e.g., four) gates for adjusting the opening size of the second opening of the shielded box.

Figure 4A:
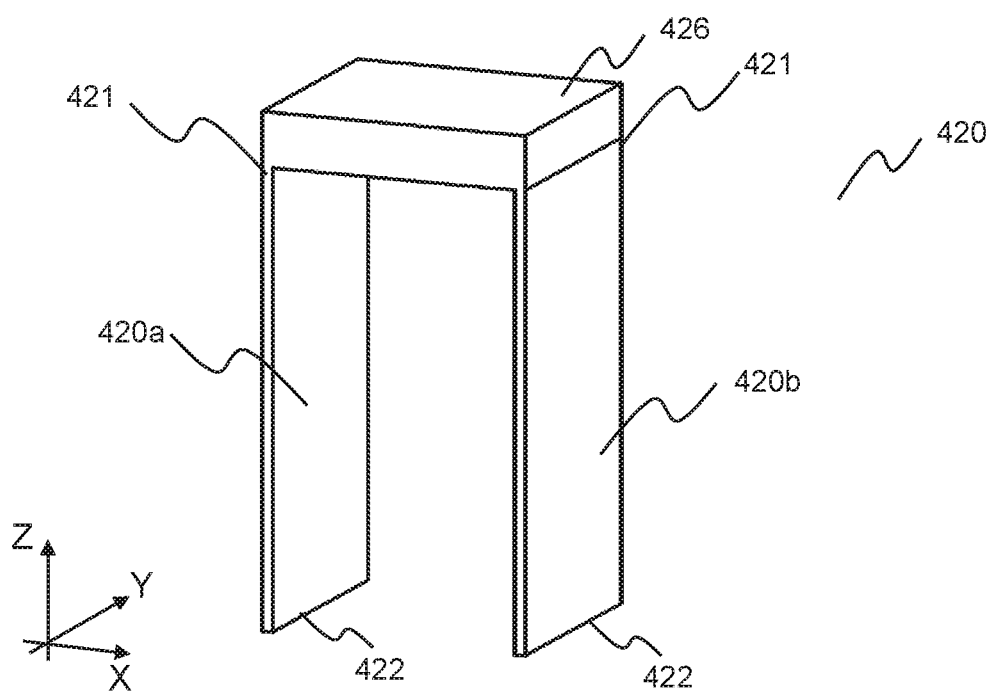
FIGS. 4A and 4B are schematic diagrams illustrating an exemplary pair of flexible plates according to some embodiments of the present disclosure.
Figure 4B:
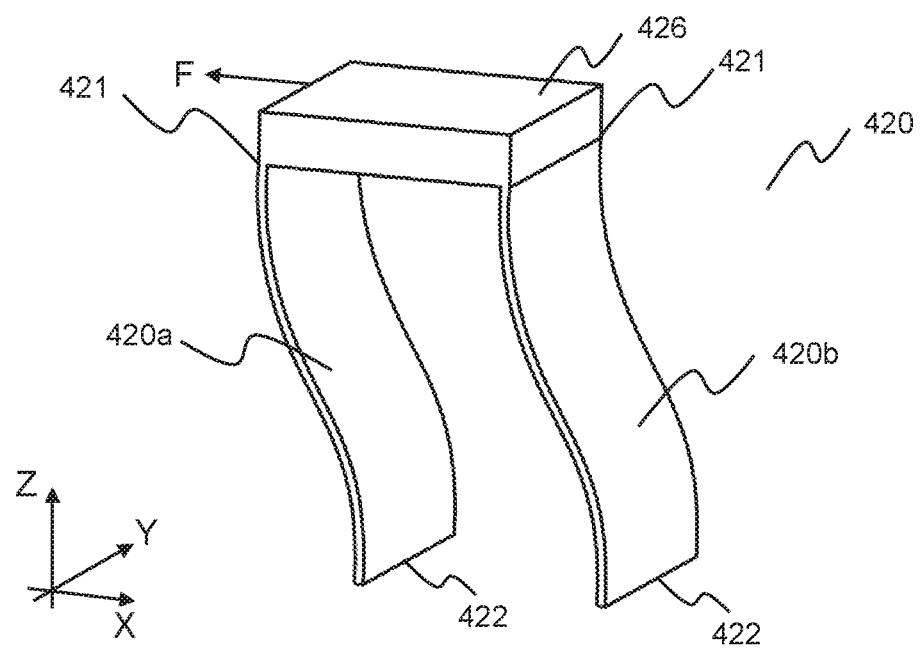

FIGS. 4A and 4B are schematic diagrams illustrating an exemplary pair of flexible plates according to some embodiments of the present disclosure. As shown in FIGS. 4A and 4B, the pair of flexible plates 420 may include a first flexible plate 420a and a second flexible plate 420b. In some embodiments, the first flexible plate 420a and the second flexible plate 420b may have the same dimension. For example, the shape, length, width, and/or thickness of the first flexible plate 420a may be the same as the second flexible plate 420b. In some embodiments, the first flexible plate 420a and/or the second flexible plate 420b may have a shape of a rectangle, a square, a round, an oval, or an arbitrary polygon, or the like, or a combination thereof. In some embodiments, the length, width, and/or thickness of the two flexible plates may be determined or adjusted according to different situations. For example, the length and/or width of the two flexible plates may be determined by available space of a collimation assembly (e.g., the collimation assembly 115, the collimation assembly 300 shown in FIG. 3, the collimation assembly 600 shown in FIG. 6, the collimation assembly 700 shown in FIG. 7, the collimation assembly 800 shown in FIG. 8). As another example, the thickness of the two flexible plates may be selected based on a stress limit of the material (e.g., the fatigue limit of steel), and/or the length (or the travel range) of a collimator device (e.g., the first movable gate 310a shown in FIG. 3, the collimator device 610 shown in FIG. 6, the collimator device 710 shown in FIG. 7, the collimator device 810 shown in FIG. 8, or the like). As a further example, the length, width, and/or thickness of the two flexible plates may be selected based on the spring rate of the two flexible plates in combination with the travel range of the collimator device. In some embodiments, the first flexible plate 420a and the second flexible plate 420b may include the same material. In some embodiments, each flexible plate of the pair of flexible plates 420 may include an elastic material. In some embodiments, the elastic material may include spring steels, elastomer, rubber, or the like, or a combination thereof. The spring steels may include carbon spring steel or alloy spring steel. The elastomer may include a thermosetting elastomer or thermoplastic elastomer (TPE). The rubber may include natural rubber, neoprene rubber, styrene butadiene rubber, or the like, or a combination thereof. For example, the pair of flexible plates 420 may include a spring steel plate.

In some embodiments, the pair of flexible plates 420 may be connected to a connecting piece 426. As shown in FIGS. 4A and 4B, a first end 421 of each flexible plate of the pair of flexible plates 420 may be connected to the connecting piece 426. In some embodiments, the pair of flexible plates 420 and the connecting piece 426 may be configured as one single piece. In some embodiments, the connecting piece 426 may be fixed onto the collimator device. In some embodiments, the connecting piece 426 may be part of the collimator device. In some embodiments, a second end 422 of each flexible plate of the pair of flexible plates 420 may be connected to a base frame (not shown).

As shown in FIG. 4A, the pair of flexible plates 420 may maintain a natural state (e.g., straight or flat) if there is no driving force applied to the connecting piece 426. As shown in FIG. 4B, the pair of flexible plates 420 may be deformed based on a driving force F applied to the connecting piece 426 along the X-axis direction. In some embodiments, the driving force F may include either a pulling force or a pushing force along the X-axis direction. Therefore, the pair of flexible plates 420 may be deformable in the X-axis direction. With the deformation of the pair of flexible plates 420, the connecting piece 426 may move along the X-axis direction, and accordingly, the pair of flexible plates 420 may guide the movement of the collimator device.

Figure 5:
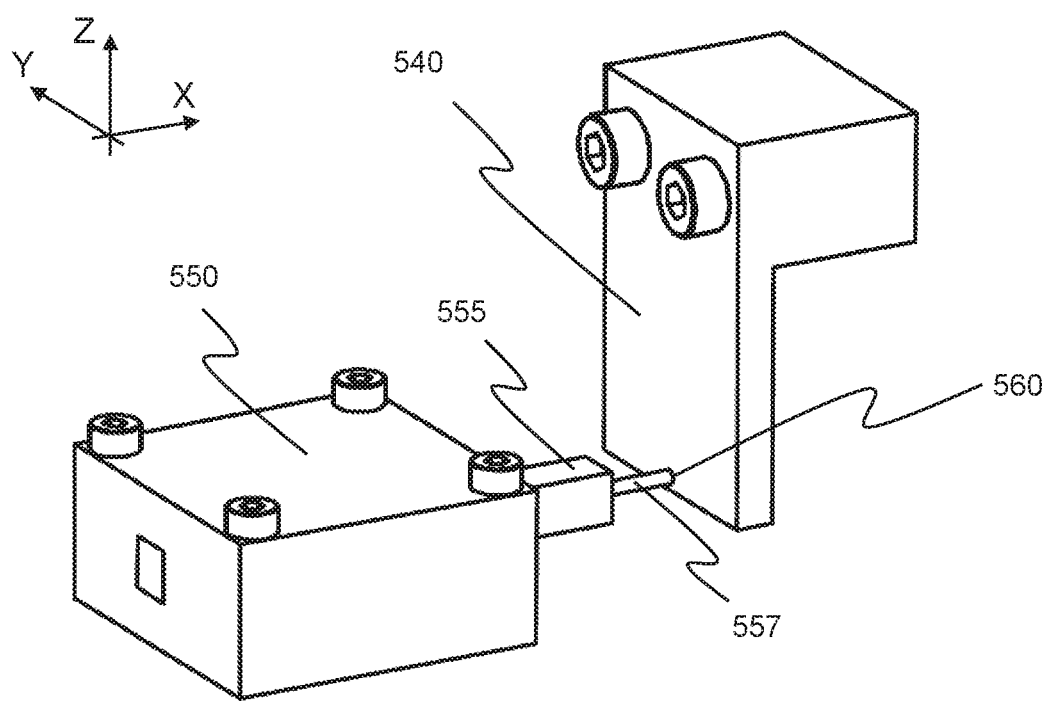
FIG. 5 is a schematic diagram illustrating an exemplary drive assembly according to some embodiments of the present disclosure.

FIG. 5 is a schematic diagram illustrating an exemplary drive assembly according to some embodiments of the present disclosure. As shown in FIG. 5, the drive assembly 550 may include a linear motor or a piezoelectric actuator. The drive assembly 550 may include a motor plunger 555. The motor plunger 555 may be configured to transmit a driving force to a collimator device (or the connector 540). The collimator device may be a movable (or adjustable) gate or a movable (or adjustable) filter described elsewhere in the present disclosure. In some embodiments, the motor plunger 555 may be connected to the connector 540 via a transmission part. In some embodiments, the transmission part may be a plate. In some embodiments, the normal of the plate may be in a direction that is substantially perpendicular to the driving force (e.g., the Y-axis direction, the Z-axis direction). In some embodiments, the transmission part may be a rod flexure 557. For example, one end of the rod flexure 557 may be fixed onto the motor plunger 555 through, for example, a threaded connection, glue joint, bonding, bolted connection, or the like, or a combination thereof. The other end of the rod flexure 557 may be connected to the connector 540 through a, for example, threaded connection, glue joint, bonding, bolted connection, or the like, or a combination thereof. In some embodiments, the other end of the rod flexure 557 may be in contact with, other than being fixed onto, the connector 540.

In some embodiments, the rod flexure 557 may be made of an elastic material. In some embodiments, the transmission part (e.g., the rod flexure 557) may deform during the movement of the collimator device. In some embodiments, the rod flexure 557 may deform due to a variance between the drive assembly 550 and a trajectory of the collimator device. Merely by way of example, as shown in FIG. 6, if the drive assembly 650 is aligned in the X-axis direction, and the driving force is in the X-axis direction, the collimator device 610 may move in the X-axis direction. In some embodiments, the collimator device 610 may have a relatively small displacement in the Y-axis direction during the movement of the collimator device 610 in the X-axis direction, and then the rod flexure 557 may deform due to the displacement of the collimator device 610 in the Y-axis direction. The displacement of the collimator device 610 in a direction (e.g., the Y-axis direction) different from that of the driving force (e.g., the X-axis direction) may be generated due to one or more factors including for example, inaccuracy of the drive assembly 550 with respect to the X-axis direction, natural bending of the flexible plates, etc. In some embodiments, as illustrated above, the transmission part may be a plate instead of the rod flexure 557. Similar to the rod flexure 557, the plate may deform due to variance(s) between the drive assembly 550 and the trajectory of the collimator device. In some embodiments, spring rate differences of flexible rate pairs may cause the collimator device to rotate about the Z-axis during trajectory in the X-axis direction. In some embodiments, a plate connection parallel to the X-Y plane may resist rotation of the collimator device while allowing displacements in the Y-axis direction. It should be noted that because of the deformation characteristics, the transmission part may support or tolerate possible spring rate differences between the flexible plate pairs, possible mechanical errors of the flexible plates, etc., so that the stability of the movement of the collimator device 610 may be improved.

In some embodiments, with the use of the rod flexure 557, the connection between the drive assembly 550 and the connector 540 may be stable and/or permanent. In some embodiments, with the use of the rod flexure 557, there may be no drive backlash (or hysteresis) when the drive assembly 550 drives the movement of the connector 540. In some embodiments, with the use of the rod flexure 557, no wear will be produced in the collimation assembly, which may improve the service life of the motion guidance assembly.

As shown in FIG. 5, a stress point 560 on the connector 540 associated with the driving force may be located at a position on the connector 540 where the rod flexure 557 connects to or is in contact with the connector 540. The stress point 560 may be located at any reasonable position of the connector 540. In some embodiments, the stress point 560 on the connector 540 may be at a substantially half height of each flexible plate of a pair of flexible plates (e.g., the pair of flexible plates shown in FIG. 3, the pairs of flexible plates 620, 625 shown in FIG. 6, the pairs of flexible plates 720, 722, 724, 726 shown in FIG. 7, the group of flexible plates 820 shown in FIG. 8), which may eliminate or reduce the bending moment load of the pair of flexible plates.

It should be noted that the above description of the drive assembly 550 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the rod flexure 557 may be omitted, and the motor plunger 555 may be connected to the connector 540 directly. As another example, the connector 540 may be configured as a portion of the drive assembly 550 (e.g., the motor plunger 555 and the connector 540 may form a single piece).

FIG. 6 is a schematic diagram illustrating an exemplary collimation assembly according to some embodiments of the present disclosure. As shown in FIG. 6, the collimation assembly 600 may include a collimator device 610, a first pair of flexible plates 620, a second pair of flexible plates 625, a base frame 630, a connector 640, and a drive assembly 650. The collimator device 610 may be similar to the collimator device illustrated in FIG. 3. The first pair of flexible plates 620 and the second pair of flexible plates 625 may be similar to the pair of flexible plates illustrated in FIG. 3 and/or the pair of flexible plates 420 shown in FIG. 4. The connector 640 may be similar to the connector 340 illustrated in FIG. 3 and/or the connector 540 shown in FIG. 5. The drive assembly 650 may be similar to the drive assembly 350 illustrated in FIG. 3 and/or the drive assembly 550 shown in FIG. 5. The base frame 630 may be similar to the base frame 330 illustrated in FIG. 3.

As shown in FIG. 6, the first pair of flexible plates 620 may include a first flexible plate and a second flexible plate. In some embodiments, the first flexible plate and the second flexible plate may have the same dimension and/or may include the same material. In some embodiments, the first flexible plate and the second flexible plate may be positioned in parallel on opposite sides of the collimator device 610 (e.g., a movable gate). The second pair of flexible plates 625 may include a third flexible plate and a fourth flexible plate. In some embodiments, the third flexible plate and the fourth flexible plate may also be positioned in parallel on opposite sides of the collimator device 610 (e.g., the movable gate). In this case, a first end of each flexible plate of the first pair of flexible plates 620 may be connected to a first end of the collimator device 610. A second end of each flexible plate of the first pair of flexible plates 620 may be fixed onto the base frame 630. A first end of each flexible plate of the second pair of flexible plates 625 may be connected to a second end of the collimator device 610. A second end of each flexible plate of the second pair of flexible plates 625 may be fixed onto the base frame 630.

In some embodiments, a connector 640 may be connected to a side of the collimator device 610. The connector 640 may be configured to transmit a driving force generated by the drive assembly 650 to the collimator device 610. In some embodiments, as shown in FIG. 6, the distance between the connector 640 and the first end of the collimator device 610 may be the same (or substantially the same) as the distance between the connector 640 and the second end of the collimator device 610. In some embodiments, a stress point on the connector 640 associated with the driving force generated by the drive assembly 650 may be at a half (or substantially half) height of each flexible plate of the first pair of flexible plates 620 and the second pair of flexible plates 625.

It should be noted that the above description of the collimation assembly 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, both flexible plates of the first pair of flexible plates 620 may be positioned on one side of the collimator device 610. As another example, both flexible plates of the second pair of flexible plates 625 may be positioned on one side of the collimator device 610. As a further example, each flexible plate of the first pair of flexible plates 620 and the second pair of flexible plates 625 may be positioned on the same side of the collimator device 610. As a further example, one flexible plate of the first pair of flexible plates 620 and one flexible plate of the second pair of flexible plates 625 may be omitted, and the other flexible plate of the first pair of flexible plates 620 and the other flexible plate of the second pair of flexible plates 625 may be positioned on different sides of the collimator device 610.

FIG. 7 is a schematic diagram illustrating an exemplary collimation assembly according to some embodiments of the present disclosure. As shown in FIG. 7, the collimation assembly 700 may include a collimator device 710, a first pair of flexible plates 720, a second pair of flexible plates 722, a third pair of flexible plates 724, a fourth pair of flexible plates 726, a base frame 730, a connector 740 and a drive assembly 750. The collimator device 710 may be similar to the collimator device illustrated in FIG. 3. The first pair of flexible plates 720, the second pair of flexible plates 722, the third pair of flexible plates 724, and the fourth pair of flexible plates 726 may be similar to the pair of flexible plates illustrated in FIG. 3 and/or the pair of flexible plates 420 shown in FIG. 4. The connector 740 may be similar to the connector 340 illustrated in FIG. 3 and/or the connector 540 shown in FIG. 5. The drive assembly 750 may be similar to the drive assembly 350 illustrated in FIG. 3 and/or the drive assembly 550 shown in FIG. 5. The base frame 630 may be similar to the base frame 330 illustrated in FIG. 3.

As shown in FIG. 7, the first pair of flexible plates 720 may include a first flexible plate and a second flexible plate. In some embodiments, the first flexible plate and the second flexible plate may have the same dimension and/or may include the same material. In some embodiments, the first flexible plate and the second flexible plate may be positioned in parallel on opposite sides of the collimator device 710 (e.g., a movable gate). The second pair of flexible plates 722 may include a third flexible plate and a fourth flexible plate. In some embodiments, the third flexible plate and the fourth flexible plate may also be positioned in parallel on opposite sides of the movable gate.

In some embodiments, a first end of each flexible plate of the first pair of flexible plates 720 may be connected to a first end of the collimator device 710. A first end of each flexible plate of the third pair of flexible plates 724 may be fixed onto the base frame 730 (e.g., via a connecting piece 731). A second end of each flexible plate of the first pair of flexible plates 720 and a second end of each flexible plate of the third pair of flexible plates 724 may be connected through a first connecting piece 760. As shown in FIG. 7, the third pair of flexible plates 724 and one flexible plate of the first pair of flexible plates 720 may be positioned on the same side of the collimator device 710. Another flexible plate of the first pair of flexible plates 720 may be positioned on an opposite side of the collimator device 710.

In some embodiments, a first end of each flexible plate of the second pair of flexible plates 722 may be connected to a second end of the collimator device 710. A first end of each flexible plate of the fourth pair of flexible plates 726 may be fixed onto the base frame 730 (e.g., via a connecting piece 732). A second end of each flexible plate of the second pair of flexible plates 722 and a second end of each flexible plate of the fourth pair of flexible plates 726 may be connected to a second connecting piece 765. As shown in FIG. 7, the fourth pair of flexible plates 726 and one flexible plate of the second pair of flexible plates 722 may be positioned on the same side of the collimator device 710. Another flexible plate of the second pair of flexible plates 722 may be positioned on an opposite side of the collimator device 710.

In some embodiments, the first connecting piece 760 and the second connecting piece 765 may be made of hard materials. Exemplary hard materials may include aluminum, steel, alloy, plastic, wood, or the like, or a combination thereof. With the first connecting piece 760, the first pair of flexible plates 720 may operate in combination with the third pair of flexible plates 724 to guide the movement of the collimator device 710. With the second connecting piece 765, the second pair of flexible plates 722 may operate in combination with the fourth pair of flexible plates 726 to guide the movement of the collimator device 710. For example, if a driving force is applied to the collimator device 710 along the X-axis direction, the collimator device 710 may move along the X-axis direction, the first pair of flexible plates 720, the second pair of flexible plates 722, the third pair of flexible plates 724, and the fourth pair of flexible plates 726 may deform in the X-axis direction, and the deformation of the four pairs of flexible plates may guide the movement of the collimator device 710.

In some embodiments, the connection between the first pair of flexible plates 720 and the third pair of flexible plates 724, or the connection between the second pair of flexible plates 722 and the fourth pair of flexible plates 726 may be regarded as a series connection. The connection between the first pair of flexible plates 720 and the second pair of flexible plates 722 may be regarded as a parallel connection. A series connection used herein refers that two or more pairs of flexible plates are connected directly or indirectly to a same site of the collimator device 710. A parallel connection used herein refers that two or more pairs of flexible plates are connected directly or indirectly to different sites of the collimator device 710. In some embodiments, there may be one or more additional pairs of flexible plates that are in series connection and/or parallel connection with the collimator device 710. For example, another pair of flexible plates may be in series connection with the third pair of flexible plates 724. As another example, another pair of flexible plates may be connected to the collimator device 710, being connected in parallel with the first pair of flexible plates 720 and the second pair of flexible plates 722.

In some embodiments, with the use of the series connection, the travel range of the collimator device 710 may be increased. As shown in FIG. 6, a deformation of the first pair of flexible plates 620 may induce a displacement of the collimator device 610 relative to the base frame 630. As shown in FIG. 7, a deformation of the first pair of flexible plates 720 may induce a displacement of the collimator device 710 relative to the first connecting piece 760, and a deformation of the third pair of flexible plates 724 may induce a displacement of the first connecting piece 760 relative to the base frame 730. The displacement of the collimator device 710 relative to the base frame 730 may be a sum of the displacement of the collimator device 710 relative to the first connecting piece 760 and the displacement of the first connecting piece 760 relative to the base frame 730. Therefore, the travel range of the collimator device 710 may be increased. In other words, if there is a series connection between the first pair of flexible plates 720 and the third pair of flexible plates 724, the travel range of the collimator device 710 may be determined based on the combination of the travel range of the first pair of flexible plates 720 and the third pair of flexible plates 724. In some embodiments, with the use of the parallel connection, the stiffness (or strength) of the collimation assembly may be improved. For example, as shown in FIG. 7, two ends of the collimator device 710 may be guided to move based on the deformation of the first pair of flexible plates 720 and the second pair of flexible plates 722, respectively.

It should be noted that the above description of the collimation assembly 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the first pair of flexible plates 720 and the third pair of flexible plates 724 may be omitted, or the second pair of flexible plates 722 and the fourth pair of flexible plates 726 may be omitted. As another example, each flexible plate of the first pair of flexible plates 720 may be positioned on the same side of the collimator device 710. As a further example, each flexible plate of the second pair of flexible plates 722 may be positioned on the same side of the collimator device 710.

FIG. 8 is a schematic diagram illustrating an exemplary collimation assembly according to some embodiments of the present disclosure. As shown in FIG. 8, the collimation assembly 800 may include a collimator device 810 and a group of flexible plates 820. The collimator device 810 may be similar to the collimator device illustrated in FIG. 3. Each flexible plate of the group of flexible plates 820 may be similar to one flexible plate of the pair of flexible plates illustrated in FIG. 3 and/or one flexible plate of the pair of flexible plates 420 shown in FIG. 4.

In some embodiments, the group of flexible plates 820 may include at least two flexible plates that are positioned in parallel. For example, as shown in FIG. 8, the group of flexible plates 820 may include four flexible plates. The four flexible plates may be positioned in parallel on the same side of the collimator device 810. In some embodiments, one end of each flexible plate of the group of flexible plates 820 may be connected to one end of the collimator device 810. The other end of each flexible plate of the group of flexible plates 820 may be fixed on a based frame (not shown in FIG. 8). The deformation of the group of flexible plates 820, based on a driving force, may guide the movement of the collimator device 810. In some embodiments, the collimator device 810 may be driven by the driving force to move along the X-axis direction, and accordingly, the group of flexible plates 820 may be deformable in the X-axis direction and may guide the movement of the collimator device 810. In some embodiments, the driving force may be generated by a drive assembly. The drive assembly may be similar to the drive assembly described elsewhere in the present disclosure (e.g., FIGS. 3 and 5, and the descriptions thereof).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A motion guidance assembly for guiding the motion of a collimator device, comprising:
    a first pair of flexible plates connected to the collimator device, wherein
        the first pair of flexible plates are deformable in a direction perpendicular to an opening of the collimator device, and
        a deformation of the first pair of flexible plates, based on a driving force, guides the motion of the collimator device.

2. The motion guidance assembly of claim 1, wherein the first pair of flexible plates include a first flexible plate and a second flexible plate, the first flexible plate and the second flexible plate having a same dimension and including a same material.

3. The motion guidance assembly of claim 2, wherein the first flexible plate and the second flexible plate are positioned in parallel on opposite sides of the collimator device.

4. The motion guidance assembly of claim 2, wherein the first flexible plate and the second flexible plate are positioned in parallel on a same side of the collimator device.

5. The motion guidance assembly of claim 1, wherein
    a first end of each flexible plate of the first pair of flexible plates is connected to a first end of the collimator device; and
    a second end of each flexible plate of the first pair of flexible plates is fixed onto a base frame.

6. The motion guidance assembly of claim 5, wherein
    a connector is connected to the first end of the collimator device, wherein the connector being configured to transmit the driving force to the collimator device to drive the motion of the collimator device.

7. The motion guidance assembly of claim 1, further comprising a second pair of flexible plates connected to the collimator device, wherein
    the second pair of flexible plates are deformable in the direction perpendicular to the opening of the collimator device.

8. The motion guidance assembly of claim 7, wherein the second pair of flexible plates include a third flexible plate and a fourth flexible plate, the third flexible plate and the fourth flexible plate being positioned in parallel on opposite sides of the collimator device.

9. The motion guidance assembly of claim 7, wherein
    a first end of each flexible plate of the first pair of flexible plates is connected to a first end of the collimator device;
    a second end of each flexible plate of the pair of flexible plates is fixed onto a base frame;
    a first end of each flexible plate of the second pair of flexible plates is connected to a second end of the collimator device;
    a second end of each flexible plate of the second pair of flexible plates is fixed onto the base frame; and
    a connector is connected to a side of the collimator device, a distance between the connector and the first end of the collimator device being substantially the same as a distance between the connector and the second end of the collimator device, the connector being configured to transmit the driving force to the collimator device to drive the motion of the collimator device.

10. The motion guidance assembly of claim 9, wherein a stress point on the connector associated with the driving force is at a substantially half height of each flexible plate of the first pair of flexible plates or the second pair of flexible plates.

11. The motion guidance assembly of claim 1, further comprising a third pair of flexible plates deformable in the direction perpendicular to the opening of the collimator device, wherein
    a first end of each flexible plate of the first pair of flexible plates is connected to a first end of the collimator device;
    a first end of each flexible plate of the third pair of flexible plates is fixed onto a base frame; and
    a second end of each flexible plate of the first pair of flexible plates and a second end of each flexible plate of the third pair of flexible plates are connected through a first connecting piece.

12. The motion guidance assembly of claim 11, wherein the third pair of flexible plates and one flexible plate of the first pair of flexible plates are positioned on a same side of the collimator device, while another flexible plate of the first pair of flexible plates is positioned on an opposite side of the collimator device.

13. The motion guidance assembly of claim 11, further comprising a second pair of flexible plates and a fourth pair of flexible plates, the second pair of flexible plates and the fourth pair of flexible plates being deformable in the direction perpendicular to the opening of the collimator device, wherein
a first end of each flexible plate of the second pair of flexible plates is connected to a second end of the collimator device;
a first end of each flexible plate of the fourth pair of flexible plates is fixed onto the base frame; and
a second end of each flexible plate of the second pair of flexible plates and a second end of each flexible plate of the fourth pair of flexible plates are connected to a second connecting piece.

14. The motion guidance assembly of claim 1, wherein the first pair of flexible plates include spring steel plates.

15. A collimation assembly, comprising:
a shielded box configured to collimate a plurality of radiation rays, the shielded box including a first opening and a second opening, the first opening being configured to allow a first portion of the plurality of radiation rays to enter the collimation assembly, the second opening being configured to allow a second portion of the plurality of radiation rays to leave the collimation assembly, the first portion of the plurality of radiation rays including the second portion of the plurality of radiation rays;
a movable gate configured to adjust an opening size of the second opening, the movable gate being connected to a first pair of flexible plates, a movement of the movable gate being guided by the first pair of flexible plates; and
a drive assembly configured to drive the movable gate to move in a direction associated with a deformation of the first pair of flexible plates.

16. The collimation assembly of claim 15, wherein
the first pair of flexible plates include a first flexible plate and a second flexible plate, the first flexible plate and the second flexible plate having a same dimension and including a same material; and
the first flexible plate and the second flexible plate are positioned in parallel on opposite sides of the movable gate.

17. The collimation assembly of claim 15, wherein
a first end of the movable gate is connected to a first end of each flexible plate of the first pair of flexible plates;
a second end of each flexible plate of the first pair of flexible plates is fixed onto a base frame; and
a connector is connected to the first end of the movable gate, the connector being configured to transmit a driving force generated by the drive assembly to the movable gate to drive the movable gate to move.

18. The collimation assembly of claim 15, further comprising a connector and a transmission part, wherein
the connector is configured to transmit a driving force generated by the drive assembly to the movable gate to drive the movable gate to move; and
the transmission part is configured to transmit the driving force from the drive assembly to the connector.

19. The collimation assembly of claim 15, wherein the drive assembly includes a linear motor or a piezoelectric actuator.

20. A radiation imaging system, comprising:
a radiation source configured to emit radiation rays;
a collimation assembly configured to collimate the emitted radiation rays;
one or more radiation detectors configured to generate measurement data in response to at least a portion of the emitted radiation rays;
a controller configured to control one or more of the radiation source, the collimation assembly and the one or more radiation detectors; and
one or more processors configured to generate an image based on the measurement data, wherein
the collimation assembly includes:
a shielded box configured to collimate a plurality of radiation rays, the shielded box including a first opening and a second opening, the first opening being configured to allow a first portion of the plurality of radiation rays to enter the collimation assembly, the second opening being configured to allow a second portion of the plurality of radiation rays to leave the collimation assembly, the first portion of the plurality of radiation rays including the second portion of the plurality of radiation rays;
a movable gate configured to adjust an opening size of the second opening, the movable gate being connected to a first pair of flexible plates, a movement of the movable gate being guided by the first pair of flexible plates; and
a drive assembly configured to drive the movable gate to move in a direction associated with a deformation of the first pair of flexible plates.

* * * * *